(12) United States Patent
Chang

(10) Patent No.: US 7,105,687 B1
(45) Date of Patent: Sep. 12, 2006

(54) PROPYLENE OXIDE PURIFICATION AND RECOVERY

(75) Inventor: Te Chang, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 11/315,677

(22) Filed: Dec. 22, 2005

(51) Int. Cl.
*C07D 301/06* (2006.01)
*C07D 301/12* (2006.01)

(52) U.S. Cl. .................. 549/531; 549/533; 203/96

(58) Field of Classification Search ............... 549/531, 549/533; 203/96
See application file for complete search history.

(56) References Cited

U.S. PATENT DOCUMENTS

| | | | |
|---|---|---|---|
| 3,578,568 A | 5/1971 | Washall | 203/64 |
| 4,824,976 A | 4/1989 | Clerici et al. | 549/531 |
| 4,833,260 A | 5/1989 | Neri et al. | 549/531 |
| 5,006,206 A | 4/1991 | Shih et al. | 203/55 |
| 5,129,996 A | 7/1992 | Shih | 203/64 |
| 5,591,825 A | 1/1997 | McKnight et al. | 530/350 |
| 5,612,122 A | 3/1997 | Tsukamoto et al. | 428/216 |
| 5,646,314 A | 7/1997 | Crocco et al. | 549/531 |
| 5,849,938 A * | 12/1998 | Rueter et al. | 549/541 |
| 6,024,840 A | 2/2000 | Rueter | 203/50 |
| 6,500,311 B1 | 12/2002 | Sawyer | 204/44 |

\* cited by examiner

*Primary Examiner*—Bernard Dentz
(74) *Attorney, Agent, or Firm*—Dennis M. Kozak; William C. Long

(57) ABSTRACT

In accordance with the invention, propylene oxide is formed by reaction of propylene and hydrogen peroxide or by reaction of propylene, oxygen and hydrogen in methanol solvent, methanol and methyl formate are separated from propylene oxide by extractive distillation wherein the aqueous bottoms from methanol recovery distillation is used as extractive distillation solvent after first having been neutralized.

3 Claims, 1 Drawing Sheet

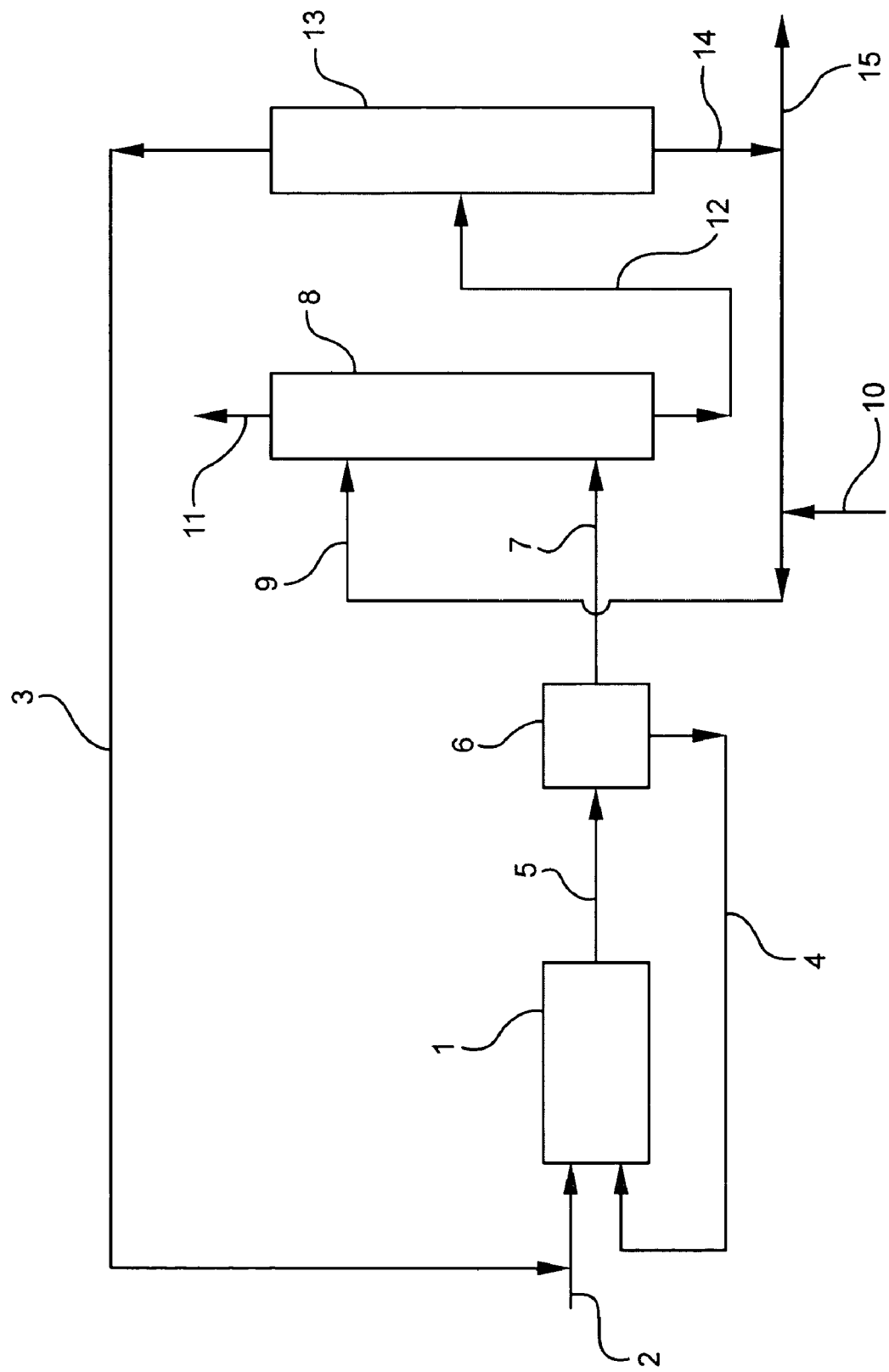

PROPYLENE OXIDE PURIFICATION AND RECOVERY

FIELD OF THE INVENTION

The present invention relates to a process for the purification and recovery of propylene oxide which is formed by the reaction of hydrogen peroxide and propylene or by reaction of propylene, oxygen and hydrogen.

DESCRIPTION OF THE PRIOR ART

The preparation of propylene oxide by reaction of propylene and hydrogen peroxide or by reaction of propylene, oxygen and hydrogen is known in the art. See, for example, U.S. Pat. Nos. 5,591,825, 4,833,260, 5,612,122, 5,646,314, 4,824,976 and many others.

Generally, this reaction to form propylene oxide is carried out in a liquid solvent comprised of methanol and water, using a solid catalyst such as TS-1 or TS-1 containing noble metal. A problem exists insofar as the separation of solvent methanol from propylene oxide requires high distillation reflux rates and the use of distillation columns comprised of a number of distillation trays. In addition, a further problem is that a key light impurity formed in the system is methyl formate which is extremely difficult to separate from propylene oxide by simple distillation but which must be removed from the product propylene oxide in order to provide an appropriate quality product.

A number of patents have addressed the problem of propylene oxide separation from methanol and other materials. U.S. Pat. No. 3,578,568 describes an extractive distillation using glycol or glycol ether extractive agent. U.S. Pat. No. 5,006,206 uses t-butanol/water as extractive distillation solvent. U.S. Pat. No. 5,129,996 uses $C_2$–$C_5$ glycol as extractive solvent. U.S. Pat. No. 6,024,840 uses methanol solvent to lower the volatility of impurities relative to propylene oxide. U.S. Pat. No. 6,500,311 separates propylene oxide and methanol by liquid—liquid extraction.

BRIEF DESCRIPTION

In accordance with the present invention, the propylene oxide containing reaction mixture resulting the reaction of hydrogen peroxide and propylene or by reaction of propylene, oxygen and hydrogen, after separation of solid catalyst, is distilled in an extractive distillation column in order to separate solvent and methyl formate from an overhead propylene oxide stream substantially reduced in impurities content. The extractive distillation solvent which is used is an aqueous bottoms stream from the solvent recovery column used in the overall process, which aqueous bottoms stream comprises methanol, water and minor amounts of heavies including glycol formed during the epoxidation. The extractive distillation solvent stream is first neutralized by addition of a basic material such as alkali metal or ammonium hydroxide before use in the distillation.

DESCRIPTION OF THE DRAWING

The attached drawing is a schematic illustration of practice of the invention.

DETAILED DESCRIPTION

Referring to the accompanying drawing, reactor 1 represents a conventional reactor which is used for the production of propylene oxide by known procedures. Reactants which may be hydrogen peroxide and propylene or propylene, oxygen and hydrogen are fed to reactor 1 via line 2. The reaction is carried out in a solvent medium which comprises methanol and which is fed to reactor 1 via line 3, and a solid TS-1 or noble metal promoted TS-1 catalyst is employed which is fed to reactor 1 via line 4.

The propylene oxide containing reaction mixture passes from reactor 1 via line 5 to separation zone 6 wherein the solid catalyst is separated and recycled with some solvent to reactor 1 via line 4. Make-up catalyst can be added as needed (not shown).

After catalyst separation, the propylene oxide containing mixture passes via line 7 to crude propylene oxide distillation column 8 which is a conventional multi stage fractional distillation column.

The propylene oxide containing mixture passing via line 7 contains about 40 to 90 wt. % methanol, about 5 to 50 wt. % water, about 1 to 10 wt. % propylene oxide, about 0.1 to 2 wt. % propylene glycol, about 0.5 to 8 wt. % to propylene glycol monomethyl ether, about 20 to 500 ppm by weight methyl formate and about 20 to 500 ppm by wt. acetaldehyde. Preferably the propylene oxide stream is depropanized (not shown) before passing to column 8. The propylene oxide stream is introduced to the lower section of distillation column 8.

The extractive distillation solvent is introduced via line 9 to the upper section of column 8. This solvent comprises about 70 to 90 wt. % water, about 1 to 15 wt. % propylene glycol, about 5 to 20 wt. % propylene glycol monomethyl ether, and about 0.5 to 2 wt. % dipropylene glycol. A soluble buffer such as sodium hydroxide, potassium hydroxide or ammonium hydroxide is added via line 10 in sufficient amount to neutralize the extractive distillation solvent stream which is slightly acidic.

Distillation column 8 is operated in conventional fashion with a purified propylene oxide stream which is substantially reduced in methanol and methyl formate recovered overhead via line 11. This stream can be further purified by conventional procedures (not shown).

The bottoms from extractive distillation column 8 passes via line 12 to methanol recovery column 13 wherein methanol solvent is distilled overhead and returned via line 3 to the epoxidation reactor 1 for further use.

An aqueous bottoms stream is removed from column 13 via line 14. A portion of this bottoms stream is recycled via line 9 to the extractive distillation for use as the extractive distillation solvent, and a portion comprising the removed methyl formate and net water made in reactor 1 is purged via line 15. The buffer material is contained in the bottoms stream and can be recovered by various means.

By the process of the invention, methanol and methyl formate can effectively be separated from the propylene oxide using readily available process streams.

It should be noted that neutralization of the extractive distillation solvent before use in column 8 is an important feature; if this stream is not neutralized, significant ring opening of the propylene oxide takes place during the extractive distillation.

The following example illustrates practice of the invention.

EXAMPLE

Reactor effluent after separation of solid catalyst and dipropanization is fed to column 8 at the rate of 18 kg/hr. Column 8 has 44 theoretical trays and the feed is introduced at tray 28 from the top. The feed composition comprises about 31 wt. % water, 54 wt. % methanol, 8.5 wt. % propylene oxide, 1.3 wt. % propylene glycol, 4.5 wt. % propylene glycol monomethyl ethers, 254 ppm by wt. methyl formate, and 254 ppm by wt. acetaldehyde.

The waste water extractive solvent stream from methanol column is fed via line 9 to column 8 at tray 8 from the top at the rate of 18 kg/hr, this solvent stream has the composition of about 81% by weight water, 6.3% by wt. propylene glycol, 11.5% by wt. propylene glycol momomethyl ethers, and 1.4% by wt. dipropylene glycols. The solvent contains soluble buffer in the ppm range as a result of neutralization of the solvent by the addition of aqueous ammonium hydroxide in an amount sufficient for the neutralization.

The extractive distillation is run at 1 atmospheric, overhead temperature of 34–35° C., bottom temperature of 86–87° C., and 0.2 reflux ratio of reflux to feed.

A propylene oxide stream is recovered overhead at the rate of 1.5% kg/hr, having a purity of 98–99% containing 55 ppm by wt. methanol and 0.02 ppm by wt. methyl formate. The stream also contains 2770 ppm by wt. acetaldehyde.

From these results it can be seen that the process of the invention provides a highly effective process for the separation of methanol and methyl formate from propylene oxide.

By comparison, a simple distillation of the same feed to tray 24 without the extractive solvent resulted in 2800 ppm by wt. methyl formate and 3000–8000 ppm by wt. methanol in the propylene oxide, even at a reflux ratio of 0.7.

I claim:

1. In a process wherein propylene oxide is formed by reaction of propylene and hydrogen peroxide or by reaction of propylene, oxygen and hydrogen in a methanol solvent, and wherein product propylene oxide is separated from methanol and methyl formate by an extractive distillation, the improvement which comprises carrying out the extractive distillation using an aqueous bottoms stream from the methanol distillation which has been neutralized by addition of a basic material as the extractive distillation solvent.

2. The process of claim 1 wherein the aqueous bottoms stream from the methanol distillation is neutralized with alkali metal or ammonium hydroxide.

3. The process of claim 1 wherein the aqueous bottoms stream from the methanol distillation is neutralized with ammonium hydroxide.

* * * * *